United States Patent
Yoshihara et al.

(10) Patent No.: US 7,153,524 B2
(45) Date of Patent: Dec. 26, 2006

(54) METHOD FOR IMPROVING ADSORPTION OF A DRUG FROM ETHYLENE OXIDE DERIVATIVE

(75) Inventors: Keiichi Yoshihara, Shizuoka (JP); Kazuhiro Sako, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 99 days.

(21) Appl. No.: 10/672,398

(22) Filed: Sep. 26, 2003

(65) Prior Publication Data

US 2005/0100607 A1    May 12, 2005

Related U.S. Application Data

(60) Provisional application No. 60/414,313, filed on Sep. 26, 2002.

(51) Int. Cl.
  *A61K 9/14*    (2006.01)
  *A61K 31/47*    (2006.01)
(52) U.S. Cl. ...................... 424/486; 514/312
(58) Field of Classification Search ............... 514/311, 514/312; 424/486
  See application file for complete search history.

(56) References Cited

U.S. PATENT DOCUMENTS

| | | | |
|---|---|---|---|
| 5,576,025 A | 11/1996 | Akiyama et al. | |
| 6,184,230 B1 * | 2/2001 | Watanabe et al. | 514/311 |
| 2001/0016577 A1 | 8/2001 | Dobrozsl et al. | |
| 2002/0028240 A1 | 3/2002 | Sawada et al. | |

FOREIGN PATENT DOCUMENTS

| | | |
|---|---|---|
| EP | 0645140 B1 | 12/1998 |
| JP | 2001-526211 A | 12/2001 |
| JP | 2003-231637 A | 8/2003 |
| WO | WO98/51306 | * 11/1998 |

* cited by examiner

*Primary Examiner*—San-Ming Hui
(74) *Attorney, Agent, or Firm*—Townsend and Townsend and Crew LLP

(57) ABSTRACT

The present invention relates to a method for improving adsorption on the gastrointestinal mucous layers of one or more selected from polyethylene glycol, polyethylene oxide, and polyoxyethylene polypropylene copolymer wherein the average number of repeating oxyethylene units of one ethylene oxide chain length is 17 or greater. It is possible to enhance pharmacological effects by using the present invention with drugs that have anti-*H. pylori* activity.

6 Claims, 3 Drawing Sheets

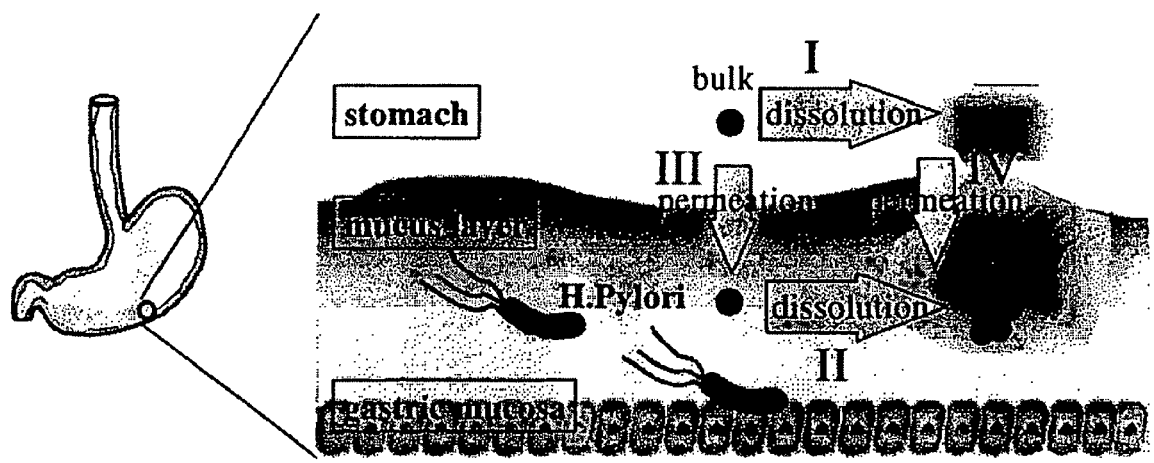
Figure 1
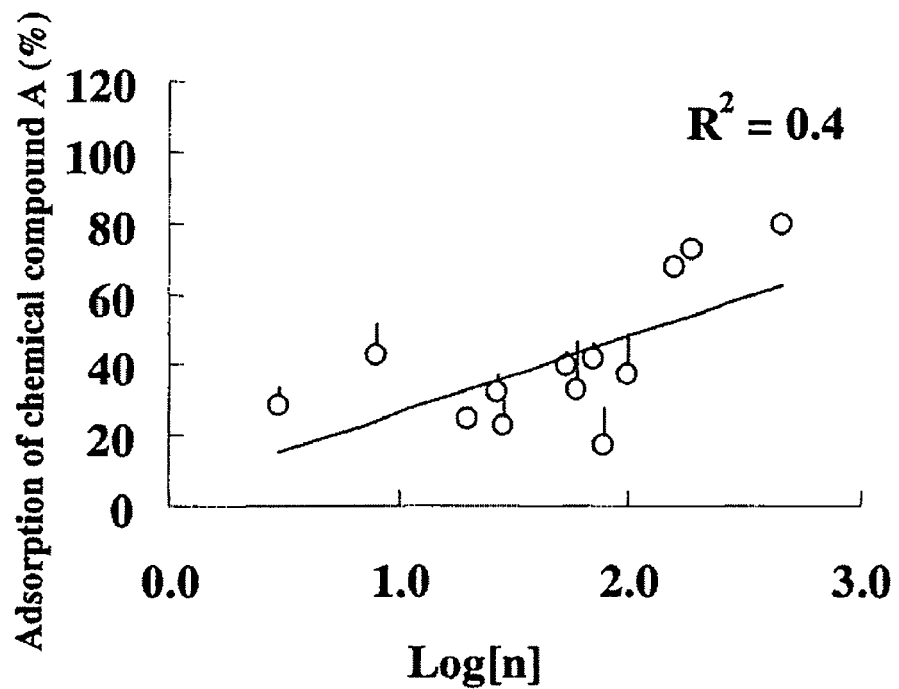
Figuare 2

METHOD FOR IMPROVING ADSORPTION OF A DRUG FROM ETHYLENE OXIDE DERIVATIVE

FIELD OF THE INVENTION

The present invention relates to a method for improving adsorption of a drug on the gastrointestinal mucous layers characterized in administration of a specific ethylene oxide derivative as the active ingredient for improving adsorption of a drug. Specifically, it relates to a method for improving adsorption of a drug on the gastrointestinal mucous layers characterized in administration as the active ingredient for improving adsorption of a drug one or more selected from polyethylene glycol, polyethylene oxide, and polyoxyethylene polypropylene copolymer where the average number of repeating oxyethylene units of one ethylene oxide chain length is 17 or greater.

PRIOR ART

The existence of *H. pylori* was ascertained from the stomach tissues of gastritis patients and since that time, *H. pylori* has been shown to participate in the morbid state of stomach and duodenal disorders, including gastritis and peptic ulcer. There have been reports of the prevention of recurrence of ulcer associated with *H. pylori*, and the importance of the eradication of *H. pylori* is now recognized. It has further been suggested that there is a cause-effect correlation between the occurrence of stomach cancer and *H. pylori* infection, even in the absence of carcinogens ([non-patent reference 1]).

Triple eradication therapy with antibiotics (amoxicillin and clarithromycin) and a proton pump inhibitor (lansoprazole) is currently the *H. pylori* eradication method of first choice. This is because acid stability of the drug is poor with singular use or concomitant use of two antibiotics due to the fact that the active optimum pH of antibiotics is generally near neutrality, and because the highest eradication rate has thus far been obtained by concomitant use of three drugs. Nevertheless, the eradication rate when 750 mg amoxicillin, 400 mg clarithromycin, and 30 mg lansoprazole are administered twice/day for one week is only 85 to 90%. Furthermore, a novel *H. pylori* eradication therapy is needed because of problems including diarrhea, development of resistant bacteria, varied doses, and reduced compliance that is attributed to the complexity of long-term treatment.

The use of 2-(2-trans-nonenyl)-3-methyl-4(1H)-quinolone derivatives (hereafter 1-hydroxy-2-(2-trans-nonenyl)-3-methyl-4(1H)-quinolone is referred to as compound A) alone or in combination with other antibiotics, and the like, and a reduction in the number of live bacteria in vivo when this compound was used alone on *H. pylori* infected animal models (Mongolian gerbils) are recited in [patent reference 1]. Nevertheless, when the use of this compound alone is considered, further augmentation of anti-*H. pylori* activity is necessary and a drug delivery technology with which compound A is made to effectively act against *H. pylori* is needed to accomplish this purpose.

*H. pylori* lives in the gastric mucus and surface layer of the gastric mucous membrane epithelial cells and in the spaces in between ([non-patent reference 2]) and therefore, it is necessary to break through the barrier effect of the mucous layers by some type of means, such as promoting adsorption of the drug on the mucous layers or improving retention, so that the drug will act directly against the *H. pylori*.

On the other hand, the ethylene oxide derivatives that are used as a base for formulation, such as polyethylene glycol, polyethylene oxide, and polyoxyethylene polypropylene copolymer, are employed as solubilizing agents, plasticizers, dispersants, and stabilizers. Polyethylene glycol is used, for instance, as a stabilizer of polypeptides, a plasticizer of sucralfate-containing compositions, and a base for retention [of a drug] in the blood. For instance, polyethylene oxide is used as a base for controlling dissolution and polyoxyethylene polypropylene copolymer, for example, Pluronic, is used as a surfactant, solubilizer, emulsifier, dispersant, and the like.

As described above, various ethylene oxide derivatives are used as bases for formulation. However, no attempts have thus far been made in connection with technology for augmenting drug activity to use ethylene oxide derivatives in order to augment adsorption of a drug on the gastrointestinal mucous layers where *H. pylori* live in order to improve adsorption of a drug on the gastrointenstinal mucous layers, and in particular, in order to augment anti-*H. pylori* activity.

Consequently, the purpose of the present invention is to provide a method of improving adsorption of a drug on the gastrointestinal mucous layers from a specific ethylene oxide derivative.

[Patent reference] U.S. Pat. No. 6,184,230

[Non-patent reference 1] T. Watanabe et al., *Gastroenterol.*, 115; 642–648 (1998)

[Non-patent reference 2] Y. Akiyama et al., Drug Delivery System, 15-3; 185–192 (2000)

DISCLOSURE OF THE INVENTION

As a result of performing intense studies under these circumstances, the inventors found that adsorption of a drug of compound A on the gastrointestinal mucous layers is high in the presence of an ethylene oxide derivative. As a result of further studies, the inventors successfully completed the present invention upon discovering that anti-*H. pylori* activity in particular is augmented when the average number of repeating oxyethylene units in the ethylene oxide derivatives is greater than 17.

That is, the present invention relates to 1. a method for improving adsorption of a drug on the gastrointestinal mucous layers, characterized in that one or more selected from polyethylene glycol, polyethylene oxide, and polyoxyethylene polypropylene copolymer where the average number of repeating oxyethylene units of one ethylene oxide chain length is 17 or greater is administered as the active ingredient for improving adsorption of a drug;

2. the method for improving adsorption of a drug on the gastrointestinal mucous layers according to above-mentioned 1, wherein the drug is an antibiotic;

3. the method for improving adsorption of a drug on the gastrointestinal mucous layers according to above-mentioned 2, whereby the drug has anti-*H. pylori* activity;

4. a pharmaceutical composition for improving adsorption of a drug on the gastrointestinal mucous layers, which contains at least a drug and one or more selected from polyethylene glycol, polyethylene oxide, and polyoxyethylene polypropylene copolymer where the average number of repeating oxyethylene units of one ethylene oxide chain length is 17 or greater;

5. the pharmaceutical composition for improving adsorption of a drug on the gastrointestinal mucous layers according to above-mentioned 4, where the drug is an antibiotic;

6. the pharmaceutical composition according to above-mentioned 5, wherein the drug has anti-*H. pylori* activity;

7. the pharmaceutical composition according to above-mentioned 4, wherein the ratio of the components of the composition when the administration form is a liquid is 0.00005% to 50% of drug and 0.1% to 37.5% of ethylene oxide derivative per total composition and/or 0.1 mg to 1 g of drug and 2 mg to 1 g of ethylene oxide derivative; and 8. the pharmaceutical composition according to above-mentioned 4, wherein the ratio of the components of the composition when the administration form is a solid is 0.01% to 95% of drug and 5% to 99.99% of ethylene oxide derivative per total composition and/or 0.1 mg to 1 g of drug and 50 mg to 1 g of ethylene oxide derivative.

As cited in the present invention, "gastrointestinal mucus" means the adhesive secretion that is secreted from the gastrointestinal mucous membrane, for instance, the mucus at the stomach walls. "Gastrointestinal mucous layers" refers to the layers of the above-mentioned gastrointestinal mucus that are formed on the surface of the gastrointestinal epithelial cells. As also cited in the present invention, "adsorption of a drug on the gastrointestinal mucous layers" means in vitro adsorption of a drug on the gastrointestinal mucus components, reflecting in vivo adsorption of the drug. For instance, it is possible to bring a lipid (oil phase) that is a component of gastrointestinal mucus and a drug suspension (aqueous phase) into contact with one another and then evaluate adsorption by determining the rate of adsorption of the drug on the lipid (refer to W. L. Agneta et al., Pharm. Res., 15; 66–71 (1998) on mucous layer composition). It appears that when adsorption is improved, "retention" in the gastrointestinal mucous layer is also improved, and there are cases in the present invention where "retention" is synonymous with adsorption. It is assumed that the ability of a drug to move to the mucous layers also improves with improvement of adsorption of a drug on the mucous layers. For convenience, "improvement of adsorption on the mucous layers" means that, for instance, the rate of adsorption of a drug on the oil phase when ethylene oxide derivative has been added to the aqueous phase is significantly increased in comparison to when ethylene oxide derivative is not added.

As cited in the present invention, "ethylene oxide derivatives" are substances containing ethylene oxide chains in the molecules thereof, and examples are polyethylene glycol, polyethylene oxides, and polyoxyethylene polypropylene copolymer. Of these, polyethylene glycol 6000 (brand name Macrogol 6000, average relative molecular weight (hereafter average molecular weight) of 8000) or polyethylene glycol 20000 (brand name Macrogol 20000, average molecular weight of 20000), polyethylene oxides (average molecular weight of 900,000 or 7,000,000), and polyoxyethylene polypropylene copolymer (brand name, Pluronic F68, Asahi Denka) are examples.

Moreover, as cited in the present invention, the "average number of repeating oxyethylene units of one ethylene oxide chain length" means the number of repeating oxyethylene units per one ethylene oxide chain within a molecule as conveniently calculated. Specifically, this is found by calculating the value obtained by dividing the number of repeating oxyethylene units of all ethylene oxide chains contained in one molecule by the structural number of ethylene oxide chains. The "structural number of ethylene oxide chains" means the number of ethylene oxide chains anywhere in the structure. For example, "the average number of repeating oxyethylene units of one ethylene oxide chain length" can be calculated as follows:

It is clear from the schematic drawing in Table 4 that there is one ethylene oxide chain in the chemical structure of Macrogol 6000. Consequently, the total number of repeating oxyethylene units (n) of ethylene oxide chains per molecule shown in Table 3 itself becomes "the average number of repeating oxyethylene units of one ethylene oxide chain length (m)." That is, the "average number of repeating oxyethylene units of one ethylene oxide chain length" of Macrogol 400, Macrogol 4000, Macrogol 6000, and Macrogol 20,000 is 8, 72, 188, and 455, respectively. Moreover, Pluronic has two ethylene oxide chains in its structure (Table 4) and therefore, the value obtained by dividing the total number of repeating oxyethylene units of ethylene oxide chains per molecule (n, Table 3) by two is "the average number of repeating oxyethylene units of one ethylene oxide chain length." That is, the total number of repeating oxyethylene units of ethylene oxide chains molecules of L31, L44, L64, P103, P85, and F68 is 3, 20, 27, 29, 54, and 160, respectively; therefore, the "average number of repeating oxyethylene units of one ethylene oxide chain length" becomes 1.5, 10, 13.5, 14.5, 27, and 80, respectively.

Adsorption of a drug on the gastrointestinal mucous layers is improved when the "average number of repeating oxyethylene units of one ethylene oxide chain length" is 17 or greater, preferably 27 or greater.

By means of the present invention, adsorptivity of compound A and 2-(2-trans-nonenyl)-3-methyl-4(1H)quinolone derivatives on the gastrointestinal mucous layers is improved. Examples of these other drugs are pharmaceutically acceptable antibiotics, including nitroimidazole antibiotics, specifically tinidazole and metronidazole; tetracyclines, specifically tetracycline, minocycline, and doxycycline; penicillins, specifically amoxicillin, ampicillin, talampicillin, bacampicillin, lenampicillin, mezlocillin, and sultamicillin; cephalosporins, specifically cefaclor, cefadroxil, cephalexin, cefpodoxime proxetil, cefixime, cefdinir, ceftibuten, cefotiam hexetil, cefetamet pivoxil, and cefuroxime axetel; penems, specifically, faropenem and ritipenem acoxil; macrolides, specifically erythromycin, oleandomycin, josamycin, midecamycin, rokitamycin, clarithromycin, roxithromycin, and azithromycin; lincomycins (for instance, lincomycin and clindamycin); aminoglycosides, specifically, paromomycin; and quinolones, specifically ofloxacin, levofloxacin, norfloxacin, enoxacin, ciprofloxacin, lomefloxacin, tosufloxacin, fleroxacin, sparfloxacin, temafloxacin, nadifloxacin, grepafloxacin, and pazfloxacin, as well as nitrofurantoin, and the like. Other examples are pharmaceutical compounds that are used to treat disease associated with stomach acid secretion, and the like, such as acid pump inhibitors, specifically omeprazole and lansoprazole; and H2 antagonists, specifically, ranitidine, cimetidine, and famotidine. Further examples include drugs used to treat hyponatremia, specifically 4'-[2-methyl-1,4,5,6-tetrahydroimidazo[4,5-d][1]benzazepin-6-yl]carbonyl]-2-phenyl-benzanilide hydrochloride; and antigastrin drugs, specifically (R)-1-[2,3-dihydro-1-(2'-methylphenacyl)-2-oxo-5-phenyl-1H-1,4-benzodiazepin-3-yl]-3-(3-methylphenyl) urea, pirenzepine hydrochloride, secretin, and proglumide. One of these drugs or a combination of two or more of these drugs can be used.

There are no special restrictions to the amount of drug used in the present invention as long as it is the amount that is effective in terms of treating disease.

It is difficult to unconditionally specify the ratio of each component when they are made into a composition. For instance, when the administration form is a liquid, such as a suspension, there is 0.00005% to 50%, preferably 0.00015% to 0.25%, particularly 0.0003% to 0.15%, of drug per entire composition. Moreover, there is 0.1% to 37.5%, preferably 0.1% to 25%, of ethylene oxide derivative per entire composition. When the administration form is a solid, such as a powder, it is possible to bring the amount of drug per entire composition to 0.01% to 95%, preferably 0.1% to 90%, of drug per entire composition, and to bring the amount of ethylene oxide derivative per entire composition to 5% to 99.99%, preferably 10% to 99.9%.

When the administration form is a liquid, it is possible to bring the amount of drug per entire composition to 0.00005% to 50%, preferably 0.0001% to 30%, and to bring the amount of ethylene oxide derivative per entire composition to 0.1% to 37.5%, preferably 1% to 25%.

There is a chance that sufficient adsorption of a drug will not be obtained if the ethylene oxide composition ratio is lower than that cited here.

With regard to the amount of each component that is used, when the administration form is a liquid, for instance, the amount of drug is brought to 1 mg to 1 g, preferably 0.5 mg to 750 mg, and the amount of ethylene oxide derivative is brought to 2 mg to 1 g, preferably 5 mg to 750 mg.

When the administration form is a solid, for instance, the amount of drug is brought to 0.1 mg to 1 g, preferably 0.5 mg to 750 mg, and the amount of ethylene oxide derivative is brought to 50 mg to 1 g, preferably 50 mg to 750 mg.

As with the composition ratio, there is a chance that sufficient adsorption of a drug will not be realized if the amount used is less than that cited here.

The ethylene oxide derivative of the present invention can be made into a pharmaceutical composition for oral use together with a drug and an appropriate filler and the like that are generally accepted pharmaceutically. There are no special restrictions to the form of the pharmaceutical preparation that this pharmaceutical composition for oral use can take, and a form that can be orally administered, including powders, tablets, capsules, liquids, suspensions, and emulsions, can be cited as an example. Formulation can be manufactured by a conventional production method.

Excipients, such as fillers, disintegrators, binders, lubricants, fluidizing agents, dispersants, suspending agents, emulsifiers, preservatives, and stabilizers, can be included in the "filler and the like that are generally accepted pharmaceutically" as cited in the present invention.

Examples of fillers are lactose, mannitol, potato starch, wheat starch, rice starch, corn starch, and crystalline cellulose; examples of disintegrators are sodium bicarbonate and sodium lauryl sulfate; examples of dispersants are crystalline cellulose, dextrin, and citric acid; examples of solubilizing agents are hydroxypropyl methylcellulose, polyoxyethylene-hydrogenated castor oil, cyclodextrins, and polysorbate 80; examples of inflating agents are carboxymethyl cellulose, carboxymethyl cellulose calcium, and croscarmellose sodium; and examples of surfactants are sodium lauryl sulfate and sucrose fatty acid ester. One or two or more can be mixed in appropriate amounts as needed.

The manufacturing method when these are made into a pharmaceutical composition for oral use involves, for instance, introducing Macrogol 6000 (polyethylene glycol 6000), drug (compound A), and filler and the like as needed to a pharmaceutically acceptable medium and thoroughly mixing these until they are dissolved or suspended. Ion-exchanged water, buffer solution or physiological saline, and the like can be selected as the pharmaceutically acceptable medium. Furthermore, this solution and/or suspension can be filled into capsules, such as gelatin capsules, to obtain a capsule form. The method whereby Macrogol 6000, compound A, and pharmaceutical filler and the like as needed are granulated by a conventional method, such as pulverizing, spray drying, freeze drying, wet granulation, or dry granulation, can be cited as a method of making a powder. Moreover, it is also possible to further add pharmaceutical filler and the like as appropriate and tablet the mixture to obtain the tablet form.

BRIEF DESCRIPTION OF THE DRAWINGS

FIG. 1 is a schematic drawing showing drug permeability in the mucous layers.

FIG. 2 is a graph showing the effect of the total number of ethylene oxide (POE) repeating oxyethylene units per molecule on the rate of adsorption of a drug on the oil phase.

BEST MODE FOR CARRYING OUT THE INVENTION

Figure 3:
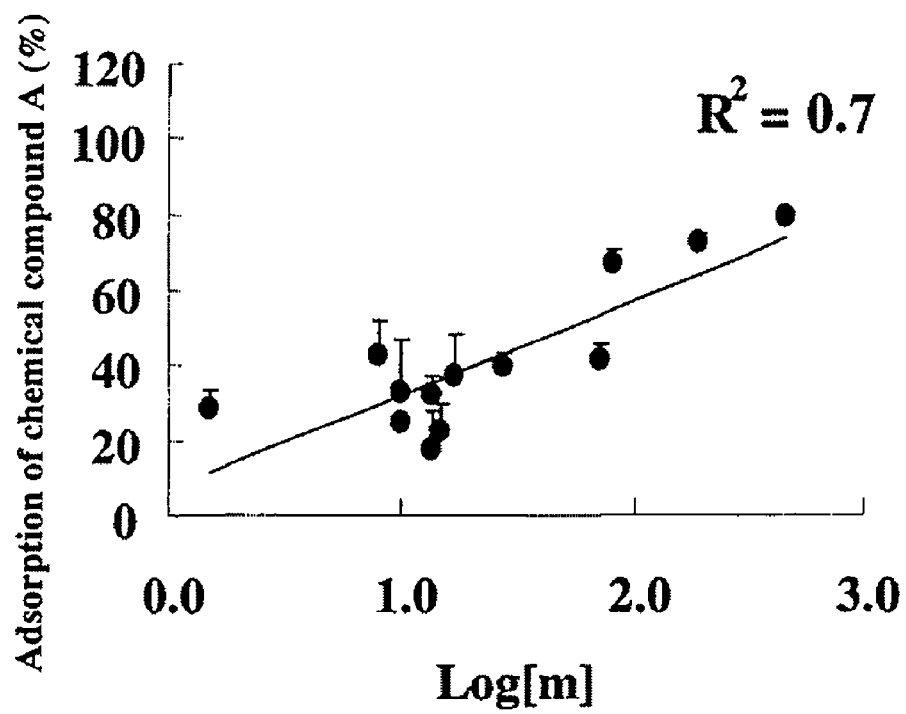
FIG. 3 is a graph showing the effect of the calculated average number of repeating oxyethylene units per ethylene oxide (POE) chain length on the rate of adsorption of a drug on the oil phase.
Figure 4:
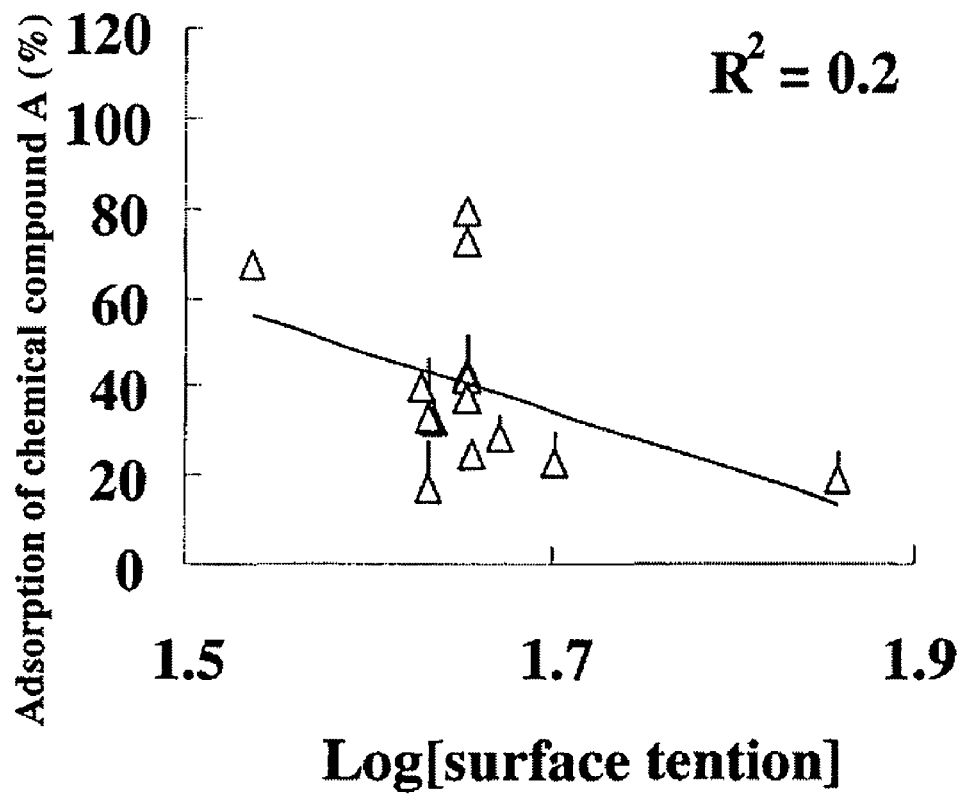
FIG. 4 is a graph showing the effect of surface tension on the rate of adsorption of a drug on the oil phase.
Figure 5:
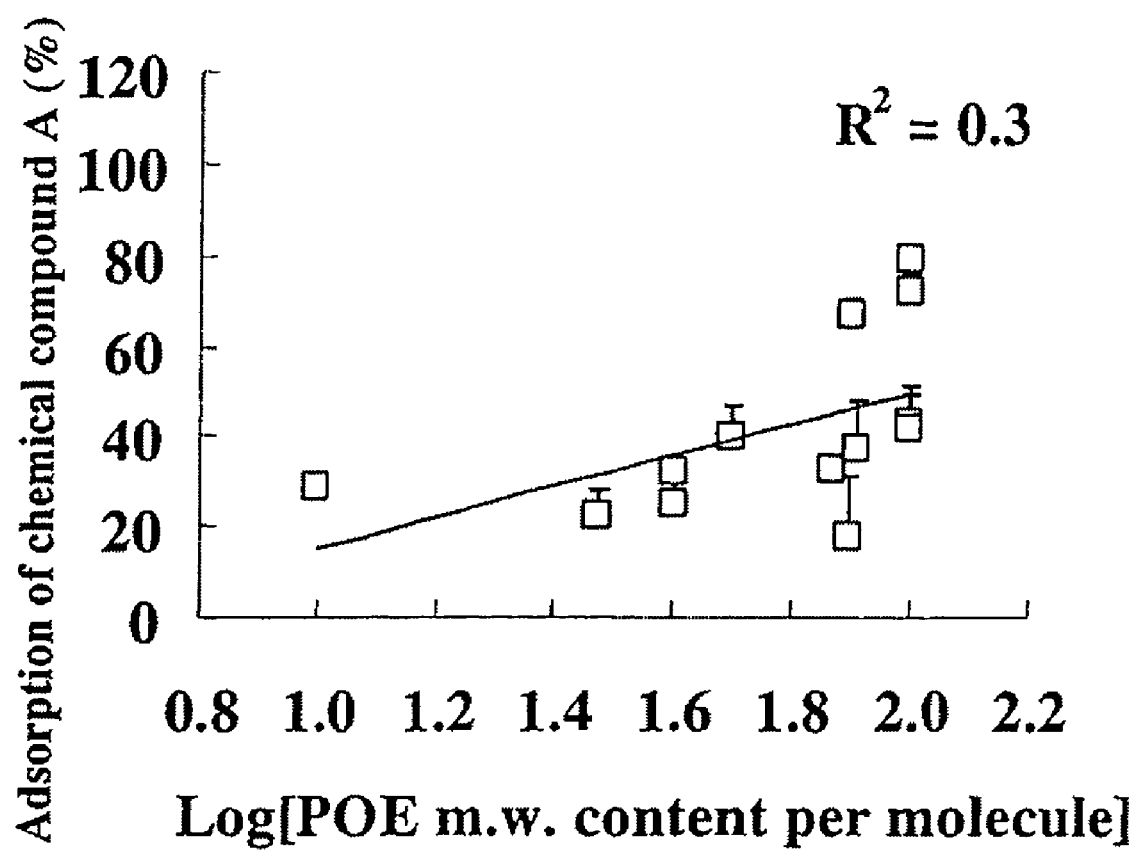
FIG. 5 is a graph showing the effect of the ethylene oxide (POE) content on the rate of adsorption of a drug on the oil phase.

The present invention will now be described in specific terms using examples, but the scope of the present invention is not limited by these examples.

EXAMPLE 1

A specific amount of compound A was added to ion-exchanged water and a drug suspension was obtained by exposure for 20 minutes to ultrasonic waves (Sono Cleaner, Kaijo Corporation). The concentration of polyethylene glycol 6000 (Sanyo Chemical Industries, Ltd.; brand name Macrogol 6000) added was adjusted to 0, 1.5%, 3.5%, 10%, 12%, and 35%.

Experiment 1

Compound A is a drug that acts directly from the gastric lumen side on the *H. pylori* that lives in the mucous layers and therefore, the case wherein after dissolution (I), the bulk powder that has been administered transfers (IV) and the case where the bulk powder is dissolved (II) after transferring to the mucous layers (III) will be considered. The effects of Macrogol 6000 on the course of dissolution of compound A were studied. A specific amount of compound A was added to ion-exchanged water, a 0.8% mucin (Sigma) solution, a 6.2% BSA (Sigma) solution, and linoleic acid (Sigma), and various drugs suspensions were obtained by exposure for 20 minutes to ultrasonic waves (Sono Cleaner, Kaijo Corporation). The rest of the procedure was performed as in Example 1 and the following samples were obtained.

[Samples]

(1) Dispersion of compound A in water (compound A concentration: 530 μg/mL)

(2) Dispersion of compound A in water (compound A concentration: 530 μg/mL)+Macrogol 6000 (3.5%)

(3) Dispersion of compound A in aqueous mucin solution (0.8%) (compound A concentration: 300 μg/mL)

(4) Dispersion of compound A in aqueous mucin solution (0.8%) (compound A concentration: 300 μg/mL)+Macrogol 6000 (3.5%)

(5) Dispersion of compound A in aqueous BSA solution (6.2%)

(6) Dispersion of compound A in aqueous BSA solution (6.2%)+Macrogol 6000 (3.5%)

(7) Dispersion of compound A in linoleic acid (8) Dispersion of compound A in linoleic acid+Macrogol 6000 (10%).

[Method]

Solubility of compound A in water was calculated by filtering the liquid after dispersion using a hydrophilic filter (0.45 μm, Advantec) and submitting the product to assay by high-performance liquid chromatography (HPLC hereafter) (n=2, sample (1); n=3, sample (2)).

Solubility of the drug in mucin was calculated by filtering the liquid after dispersion using a hydrophilic filter (0.8 μm, Advantec) and submitting the product to assay by HPLC (n=3, samples (3) and (4)).

The liquid after dispersion was filtered with a hydrophilic filter (0.45 μm, Advantec), absorbance at 370 nm and 550 nm (corrected for turbidity) was determined under room temperature using an ultraviolet-visible spectrophotometer, and solubility was calculated (n=3, samples (5) and (6)).

The liquid after dispersion was filtered with a hydrophilic filter (0.45 μm, Advantec), absorbance at 366 nm and 550 nm (corrected for turbidity) was determined under room temperature using an ultraviolet-visible spectrophotometer, and solubility was calculated (n=3, samples (7) and (8)).

[Results and Discussion]

Even though there was not a significant increase in solubility of compound A when the Macrogol 6000 was increased up to 3.5% ((2), 0.1 μg/mL) in comparison to the case where Macrogol 6000 was not added ((1), 0.1 μg/mL), when 0.2% of Macrogol 6000 was added to compound A and administered to H. pylori-infected animal models (Mongolian gerbils), augmentation of in vivo anti-H. pylori activity was seen (Example 4) in comparison to the case where Macrogol 6000 was not used. Therefore, it appears that the main reason for augmentation of in vivo anti-H. pylori activity is not improvement of drug solubility in water by the Macrogol 6000.

TABLE 1

Effect of PEG6000 on the solubility of chemical compound A in water and/or components of mucus layer

| solvent | solubility (μg/mL) | |
|---|---|---|
| distilled water | 0.1 ± 0.05 | # |
| +3.5% PEG6000 | 0.1 ± 0.04 | |
| 0.8% mucin aq. solution | 5.9 ± 1.7 | # |
| +3.5% PEG6000 | 6.9 ± 0.5 | |
| 6.2% BSA aq. solution | 18.0 ± 4.8 | * |
| +3.5% PEG6000 | 26.9 ± 1.9 | |
| linoleic acid | 135.0 | |
| +10% PEG6000 | 110.0 | |

(*; $p < 0.05$, #; not significantly different)

The mucous layers in the digestive tract comprise water, mucin, proteins and lipids (W. L. Agneta et al., Pharm. Res., 15; 66–71 (1998)); thus, the effects of addition of Macrogol 6000 on solubility of compound A in various types of mucus components were investigated (Table 1).

Although solubility of compound A in aqueous mucin solution (sample (3), 5.9 μg/mL) was markedly increased when compared to solubility in water, when Macrogol 6000 was added (sample (4), 6.9 μg/mL), the increase was only 1.2-fold. Although solubility of compound A in BSA solution as a model of a protein that comprises the mucous layers (sample (5), 18.0 μg/mL) was markedly increased when compared to solubility in water, when Macrogol 6000 was added (sample (6), 26.9 μg/mL), the increase was only 1.5-fold. It is reported that the total amount of each lipid comprising mucus is 37%, and the highest content of the lipids comprising mucus is that of linoleic acid at 24% (W. L. Agneta et al., Pharm Res., 15; 66–71 (1998)). Although solubility of compound A in linoleic acid (sample (7), 135.0 μg/mL) was markedly increased when compared to solubility in water, an increase was not seen when Macrogol 6000 was added (sample (8), 110.0 μg/mL). Based on the above-mentioned results, it can be assumed that once it has transferred to the mucous layers, compound A is easily dissolved in the mucous layers at the bactericidal concentration (concentration that is 10-fold the minimum concentration (0.025 μg/mL) at which an increase in bacteria is inhibited), but the increase in solubility of compound A in mucous components when Macrogol 6000 is added (1.2-fold to 1.5-fold) is markedly low in comparison to the increase in the amount of compound A that is adsorbed on the oil of the mucus components (2.0-fold, refer to Example 2), and it appears that Macrogol 6000 is not a main factor in the augmentation of in vivo anti-H. pylori activity (refer to Example 4).

According to the above-mentioned, it appears that the main reason for the augmentation of in vivo anti-H. pylori activity is not improvement of solubility of compound A in water or mucus components due to the addition of Macrogol 6000.

Experiment 2

[Method]

In order to study adsorption of a drug from an aqueous phase onto an oil phase (model of mucous layers), an in vitro test system wherein mixing of the oil components in the aqueous phase is prevented was constructed by immobilizing the oil phase with a gelling agent and separating it from the aqueous phase of a drug suspended in a mucin solution. Immobilization of the oil phase was performed by adding 120 mg of an oil gelling agent, which is a natural oil and fat fatty acid extracted from castor oil (Johnson Co., Ltd.), to 2 mL of medium chain fatty acid triglyceride (Nihon Oils and Fats Co., Ltd.; brand name: Panaset) and preparing an oil gel in a test tube (inner diameter of 1 cm, Eiken tube No. 5). A solution of 600 μg of compound A suspended in 2 mL of an aqueous 0.8% mucin solution was prepared and brought into contact with the oil phase (n=6). When Macrogol 6000 was added to the aqueous phase, the concentration was brought to 3.5% (n=3 to 6). After setting the solution aside for two hours, the aqueous phase was recovered and compound A was assayed by HPLC. Furthermore, the surface of the oil phase was washed with methanol and compound A in the recovered solution was assayed by HPLC.

[Results and Discussion]

When compared to the matter adhering to the surface of the oil phase when the mucin solution alone or the compound A-mucin suspension was brought into contact with the immobilized oil phase and set aside and then the aqueous phase was decanted, an increase in adhering matter was observed when Macrogol 6000 was added. When the compound A in the adhering matter was separated and assayed (Table 2), the amount of drug adsorbed at the surface of the oil phase was 259 μg (47% of the charged amount) in the case of the compound A-mucin suspension, whereas this increased to 506 μg (2.0-fold) when Macrogol 6000 was added, with an average of 93% of the drug that was added adsorbed at the surface of the oil phase. Moreover, it was confirmed that the Macrogol 6000 aggregated, apparently as a result of interaction, in the aqueous mucin solution (no drug added). Based on these facts, it was concluded that when this mucin-Macrogol 6000 aggregate produced by aggregation of Macrogol 6000 and mucin was adsorbed by the oil, the drug was retained in the aggregate and there was an increase in the amount of drug adsorbed on the oil phase. On the other hand, it was suggested that because there was not an increase in the amount of drug adsorbed on the oil phase when mucin was not added, regardless of whether or not Macrogol 6000 was added (Table 2), mucin and Macrogol 6000 must both be present in order for the amount of drug adsorbed in the oil phase to increase.

Based on the above-mentioned, it is concluded that in terms of a mechanism of augmenting the in vivo anti-*H. pylori* activity of compound A, the addition of Macrogol 6000 participates little in improvement of solubility of compound A in water or in mucus components (Table 1). Moreover, it can also be assumed that the addition of Macrogol 6000 participates little in the diffusibility of drug in the mucous layers after dissolution. Consequently, it appears that in terms of a main factor in augmenting the in vivo anti-*H. pylori* activity of compound A, compound A adsorption on mucus is improved when Macrogol 6000 aggregates with mucin and is adsorbed by the lipids (oils) that are a component of mucus.

TABLE 2

Effect of PEG6000 and mucin on the adsorption amount of chemical compound A on the oil-gel phase

| water phase | adsorption amount of chemical compound A (μg) | |
|---|---|---|
| | without PEG6000 | with 3.5% PEG6000 |
| mucin (+) | 259 ± 63 | 506 ± 53 * |
| mucin (−) | 249 ± 24 | 173 ± 25 |

(*; p < 0.01)
drug charge; 600 μg

Experiment 3
[Method]

The rate of adsorption of a drug of compound A on the oil phase was measured by the same method as in Example 2.

[Results and Discussion]

The effect of the number of repeating oxyethylene units of ethylene oxide (POE) on the rate of adsorption of a drug on the oil phase (Table 3) was investigated. In contrast to the fact that a significant increase in the adsorption rate was seen when the number of repeating oxyethylene units (n) was 72 or greater when Macrogol was added, and 54 or greater when Pluronic was added, increasing the number of repeating oxyethylene units up to 100 had no effect on the adsorption rate when hydrogenated castor oil (Japan Chemicals Co., Ltd., HCO) was added. When the correlation between the adsorption rate and the number of POE repeating oxyethylene units is analyzed (FIG. 2), the correlation coefficient is 0.4, indicating that the correlation between the two is low.

TABLE 3

Adsorption of chemical compound A on the oil-gel phase in presence of various excipients contains of polyoxyethylene (POE) units in molecule

| excipient | n | m | amount(%) |
|---|---|---|---|
| without excipient | 0 | 0 | 19 ± 7 |
| PEG400 | 8 | 8 | 42 ± 9 |
| 4000 | 72 | 72 | 42 ± 4* |

TABLE 3-continued

Adsorption of chemical compound A on the oil-gel phase in presence of various excipients contains of polyoxyethylene (POE) units in molecule

| excipient | n | m | amount(%) |
|---|---|---|---|
| 6000 | 188 | 188 | 72 ± 3* |
| 20000 | 455 | 455 | 79 ± 0* |
| Pluronic L31 | 3 | 1.5 | 28 ± 5 |
| L44 | 20 | 10 | 25 ± 2 |
| L64 | 27 | 13.5 | 32 ± 5 |
| P103 | 29 | 14.5 | 22 ± 7 |
| P85 | 54 | 27 | 40 ± 4* |
| F68 | 160 | 80 | 67 ± 3* |
| HCO 60 | 60 | 10 | 33 ± 14 |
| 80 | 80 | 13.3 | 17 ± 10 |
| 100 | 100 | 16.7 | 37 ± 11 |

*p < 0.01

TABLE 4

Chemical structures and schematic images of PEG derivatives

| PEG derivative | chemical structure |
|---|---|
| PEG polyethylene glycol | $HO(C_2H_4O)_nH$ |
| Plurronic surfactant polyoxyethylene polyoxypropylene co-polymer | $HO(C_2H_4O)_2(C_3H_6O)_c(C_2H_4O)_bH$ |
| HCO surfactant polyoxyethylene stearic acid tri-glyceride | $CH_2-O-(C_2H_4O)_a-C(=O)-R_1-CHR_2-O(C_2H_4O)_dH$ $CH-O-(C_2H_4O)_b-C(=O)-R_1-CHR_2-O(C_2H_4O)_eH$ $CH_2-O-(C_2H_4O)_c-C(=O)-R_1-CHR_2-O(C_2H_4O)_fH$ R1: $C_{10}H_{20}$ R2: $C_6H_{13}$ |

Experiment 4
[Method]

In vivo anti-*H. pylori* activity was evaluated with animal experiments using Mongolian gerbil infection models. The sample solutions were drug solutions that have been prepared by suspension of compound A using an 0.5% methylcellulose solution containing 0.2% of Macrogol 6000. The drug was administered twice a day for three days at an administration volume of 20 mL/kg using an oral stomach tube. The stomach was autopsied and excised and the number of *H. pylori* in the stomach were measured the day after the final administration. In vivo anti-*H. pylori* activity was evaluated from clearance, that is, the ratio of the number of cases in which *H. pylori* was identified and the number of cases in which the number of bacteria after treatment was below the detection limit.

[Results and Discussion]

In vivo anti-*H. pylori* activity was evaluated by animal experiments using Mongolian gerbil infection models (Table 5). The 0.5% methylcellulose suspension (MC suspension) showed clearance of 80% with a dose of 1 mg/kg. When 0.2% of Macrogol 6000 was added to the 0.5% MC suspension, clearance was 80% or greater with a dose of 0.1 mg/kg or higher, indicating that there was augmentation (10-fold) of the in vivo anti-*H. pylori* activity of compound A. The main reason for the augmented in vivo anti-*H. pylori* activity of compound A appears to be that the Macrogol 6000 aggregated with the mucin so that the drug was taken up when the aggregate was adsorbed on the lipids (oils) that are mucus components, improving mucus adsorption of compound A (refer to Table 2).

It is clear from the results in Experiments 1 through 4 that the main factor in the compound A in vivo anti-*H. pylori* activity-augmenting mechanism of Macrogol 6000 is that the Macrogol 6000 forms an aggregate with the mucin in the mucus components so that the drug is taken up when this aggregate is adsorbed on the oil that is a mucus component, with the amount of drug adsorbed in vitro on the immobilized oil phase increasing when Macrogol 6000 is added. The in vivo anti-*H. pylori* activity of compound A increased when Macrogol 6000 was added; therefore, it was shown that there is a correlation with an increase in the amount of drug adsorbed on the mucus component (oil) in vitro. Furthermore, there was also a correlation between adsorption of a drug on an oil and the average number of repeating oxyethylene units of one ethylene oxide chain length, with 17 or greater being the average number of repeating oxyethylene units of one ethylene oxide chain length with which there is a significant increase in adsorption of a drug on an immobilized oil phase.

TABLE 5

Therapeutic efficacy of chemical compound A against H. pylori infection in Mongolian gerbils

| Concentration of PEG6000(%) | Clearance rate (Clearance ratio) Dose (mg/kg) | | | | |
|---|---|---|---|---|---|
| | 0 | 0.1 | 0.3 | 1 | 3 |
| 0 | 0% (0/5) | 0% (0/5) | 20% (1/5) | 80% (4/5) | 80% (4/5) |
| 0.2 | 0% (0/5) | 80% (4/5) | 100% (4/4) | 80% (4/5) | 100% (4/4) |

Experiment 5

[Method]

The amount of various drugs adsorbed in vitro was measured using the method in Example 2. A solution of 600 µg of each compound suspended in 2 mL of an aqueous 0.8% mucin solution was prepared and brought into contact with the oil phase (n=3,6). When Macrogol 6000 was added to the aqueous phase, it was brought to 3.5% (n=3,6). After setting the solution aside for 2 hours, the aqueous phase was recovered and the drug content in the aqueous phase was found by assaying each compound with an ultraviolet-visible spectraphotometer. The compounds that were used were nifedipin, nicardipine hydrochloride, compound B, and compound C. Compound B was (R)-1-[2,3-dihydro-1-(2'-methylphenacyl)-2-oxo-5-phenyl-1H-1,4-benzodiazepin-3-yl]-3-(3-methylphenyl)urea, and compound C was 4'-[(2-methyl-1,4,5,6-tetrahydroimidazo[4,5-d][1]benzazepin-6-yl)carbonyl]-2-phenylbenzanilide hydrochloride. Furthermore, the oil phase surface was washed with methanol and the drug adsorbed on the oil phase in the recovered solution was assayed with an ultraviolet-visible spectrophotometer for each compound.

[Results and Discussion]

The amount of drug adsorption of each compound adsorbed on the surface of the oil phase when Macrogol 6000 was added increased significantly in comparison to when Macrogol 6000 was not added (Table 6). This is apparently because the drug was taken up when the aggregate of Macrogol 6000 and mucin was adsorbed on the lipid (oil) that is a mucus component.

TABLE 6

Effect of PEG6000 on the adsorption amount of various chemical compounds on the oil-gel phase (n = 3; mean ± SD)

| | adsorption amount of chemical compound(µg) | | |
|---|---|---|---|
| chemical compound | without PEG6000 | with 3.5% PEG6000 | |
| nifedipine | 429 ± 4 | 506 ± 4 | * |
| nicardipine | 47 ± 6 | 96 ± 5 | * |
| chemical compound B | 269 ± 13 | 411 ± 3 | * |
| chemical compound C # | 335 ± 10 | 370 ± 12 | * |

; n = 6, mean ± SD
600 µg loading
*; $P < 0.01$

INDUSTRIAL APPLICABILITY

The present invention relates to a method of increasing adsorption of a drug on the gastrointestinal mucous layers using an ethylene oxide derivative and makes it possible to augment the in vivo anti-*H. pylori* activity of a drug by increasing adsorption of a drug on gastrointestinal mucus. Furthermore, the present invention can be applied to singular drug eradication therapy, which has been difficult to accomplish by the current therapies for *H. pylori* eradication, and this will help to improve compliance.

The invention claimed is:

1. A method for improving adsorption of a drug on the gastrointestinal mucous layers, characterized in that one or more selected from polyethylene glycol, polyethylene oxide, and polyoxyethylene polypropylene copolymer where the average number of repeating oxyethylene units of one ethylene oxide chain length is 17 or greater is administered as the active ingredient for improving adsorption of a drug.

2. The method for improving adsorption of a drug on the gastrointestinal mucous layers according to claim 1, wherein the drug is an antibiotic.

3. A pharmaceutical composition for improving adsorption of a drug on the gastrointestinal mucous layers, which contains at least a drug and one or more selected from polyethylene glycol, polyethylene oxide, and polyoxyethylene polypropylene copolymer where the average number of repeating oxyethylene units of one ethylene oxide chain length is 17 or greater.

4. The pharmaceutical composition for improving adsorption of a drug on the gastrointestinal mucous layers according to claim 3, where the drug is an antibiotic.

5. The pharmaceutical composition according to claim 3, wherein the ratio of the components of the composition when the administration form is a liquid is 0.00005% to 50% of drug and 0.1% to 37.5% of ethylene oxide derivative per total composition and/or 0.1 mg to 1 g of drug and 2 mg to 1 g of ethylene oxide derivative.

6. The pharmaceutical composition according to claim 3, wherein the ratio of the components of the composition when the administration form is a solid is 0.01% to 95% of drug and 5% to 99.99% of ethylene oxide derivative per total composition and/or 0.1 mg to 1 g of drug and 50 mg to 1 g of ethylene oxide derivative.

* * * * *

UNITED STATES PATENT AND TRADEMARK OFFICE
CERTIFICATE OF CORRECTION

PATENT NO. : 7,153,524 B2  Page 1 of 1
APPLICATION NO. : 10/672398
DATED : December 26, 2006
INVENTOR(S) : Yoshihara et al.

It is certified that error appears in the above-identified patent and that said Letters Patent is hereby corrected as shown below:

Please delete Claim 1, col. 12 and insert therefor:

--1.   A method for improving adsorption of a drug on the gastrointestinal mucous layers, wherein the drug has anti-*H. pylori* activity, characterized in that one or more selected from a polyethylene glycol selected from the group consisting of PEG4000, PEG6000 and PEG 20000, and a polyoxyethylene polyoxypropylene copolymer selected from the group consisting of Pluronic P85 and Pluronic F68, which have an average number of repeating oxyethylene units of one ethylene oxide chain length of 27, and 80, respectively.--.

Please delete Claim 3, col. 12 and insert therefor:

--3.   A pharmaceutical composition for improving adsorption of a drug on the gastrointestinal mucous layers, wherein the drug has anti-*H. pylori* activity, and one or more selected from a polyethylene glycol selected from the group consisting of PEG4000, PEG6000 and PEG 20000, and a polyoxyethylene polyoxypropylene copolymer selected from the group consisting of Pluronic P85 and Pluronic F68, which have an average number of repeating oxyethylene units of one ethylene oxide chain length of 27, and 80, respectively.--.

Signed and Sealed this

Twenty-third Day of June, 2009

JOHN DOLL
*Acting Director of the United States Patent and Trademark Office*